United States Patent
Kulagowski

(12) 
(10) Patent No.: US 6,362,196 B1
(45) Date of Patent: Mar. 26, 2002

(54) METHOD TO TREAT PAIN UTILIZING BENZIMIDAZOLE NMDA/NR2B ANTAGONISTS

(75) Inventor: Janusz Kulagowski, Harlow (GB)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/698,422

(22) Filed: Oct. 27, 2000

Related U.S. Application Data

(60) Provisional application No. 60/162,546, filed on Oct. 29, 1999.

(51) Int. Cl.[7] ................. A61K 31/4725; A61K 31/4523
(52) U.S. Cl. .................. 514/307; 514/322; 514/338; 514/394
(58) Field of Search ................. 514/307, 322, 514/338, 394

(56) References Cited

U.S. PATENT DOCUMENTS

| | | | |
|---|---|---|---|
| 5,306,723 A | | 4/1994 | Chenard |
| 5,436,255 A | | 7/1995 | Butler |
| 5,714,498 A | * | 2/1998 | Kulagowski et al. ........ 514/307 |

FOREIGN PATENT DOCUMENTS

| | | |
|---|---|---|
| EP | 0441 506 | 1/1991 |
| EP | 0787 493 | 1/1997 |
| WO | 91/17156 | 11/1991 |
| WO | 92/18502 | 10/1992 |
| WO | 93/02052 | 2/1993 |
| WO | 96/37226 | 11/1996 |

OTHER PUBLICATIONS

A. Wenzel et al., NeuroReport, 7:45–48(1995).
S. Boyce et al., Neuropharmacology, 38:611–623(1999).
D.J. Laurie et al., Mol. Brain Res., 51:23–32(1997).
T. Ishii et al., J. Biol.Chem., 268:2836–2843(1993).
M.B. Max et al., Clin. Neuropharmacology, 18:360–368(1995).
A. H. Dickenson, TIPS, 11:307–309(1990).
K. Taniguchi et al., Brit. J. Pharmacology, 122:809–812(1992).
J. D. Kristensen et al., Pain, 51:249–253(1995).
P. K. Eide et al., Pain, 61:221–228(1995).
D. J. Knox et al., Anaesth. Intens. Cave, 23:620–622(1995).

* cited by examiner

Primary Examiner—C. S. Aulakh
(74) Attorney, Agent, or Firm—Shu M. Lee; David L. Rose

(57) ABSTRACT

Substituted benzimidazole derivatives that are NMDA NR2B antagonists are utilized to treat pain.

2 Claims, No Drawings

METHOD TO TREAT PAIN UTILIZING BENZIMIDAZOLE NMDA/NR2B ANTAGONISTS

This application claims the benefit of U.S. patent application Ser. No. 60/162,546 filed Oct. 29, 1999.

BACKGROUND OF THE INVENTION

1. Field of the Invention

This invention relates to a method of treatment of pain by utilizing NMDA NR2B antagonists. In particular, substituted benzimidazole derivatives that are NMDA NR2B antagonists are utilized to treat pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported (J. D. Kristensen, et al., *Pain*, 51:249–253 (1992); K. Eide, et al., *Pain*, 61:221–228 (1995); D. J. Knox, et al., *Anaesth. Intensive Care* 23:620–622 (1995); and M. B. Max, et al., *Clin. Neurophannacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. I. Ishii, et al., *J. Biol. Chem.*, 268:2836–2843 (1993), A. Wenel, et al., *NeuralReport*, 7:45–48 (1995), and D. J. Laurie et al., *Mol. Brain Res.*, 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. For example, S. Boyce, et al., *Neuropharnacology*, 38:611–623 (1999) describes the effect of selective NMDA NR2B antagonists on pain with reduced side-effects. Thus, it would be desirable to provide novel NMDA antagonists that target the NR2B receptor.

Phenol compounds described as NMDA antagonists are described in U.S. Pat. Nos. 5,306,723 and 5,436,255, and in International Patent Publications WO91/17156, WO92/19502, WO93/02052, WO94/29571, WO95/28057, WO96/37226, and EP 04422506. Benzyl piperidines substituted with phenols or imidazoles are described in Z.-L. Zhou, et al., *J. Medicinal Chemistry*, 42:2993–3000 (1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and *British J. Pharmacol.*, 123:463(1998). However, there continues to be a need for novel NMDA antagonists that target the NR2B receptor.

U.S. Pat. No. 5,714,498 (International Patent Publication WO94/21615) describes benzimidazole derivatives utilized as dopamine D4 antagonists.

SUMMARY OF THE INVENTION

The present invention relates to a method to treat pain, migraine, depression, anxiety, schizophrenia, Parkinson's disease, or stroke, by utilizing NMDA NR2B antagonist, substituted-benzimidazole derivatives.

DETAILED DESCRIPTION OF THE INVENTION

In one aspect, a method of this invention treats pain, migraine, depression, anxiety, schizophrenia, Parkinson's disease, or stroke, by administering NMDA NR2B antagonists described by formula (I):

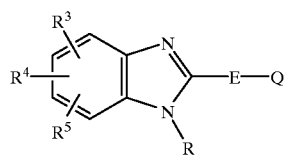

(I)

or a salt or prodrug thereof, wherein

E represents —$CH_2$— or —$CH_2CH_2$—;

R represents hydrogen or $C_{1-6}$alkyl;

Q represents a moiety of formula Qa, Qb, or Qc:

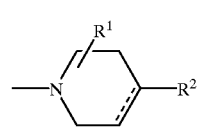

(Qa)

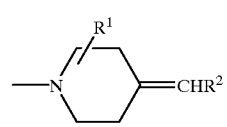

(Qb)

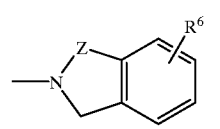

(Qc)

in which the broken line represents an optional chemical bond;

$R^1$ represents hydrogen, or an optionally substituted $C_{1-6}$alkyl, $C_{1-6}$alkoxy, $C_{2-6}$alkenyl, $C_{2-6}$alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents aryl, aryl($C_{1-6}$)alkyl, aryloxy($C_{1-6}$)alkyl, aryl(C1-6)alkyl, aryl($C_{1-6}$)alkoxy, aryl($C_{2-6}$)alkenyl, aryl ($C_{2-6}$)alkynyl, heteroaryl or heteroaryl($C_{2-6}$)alkenyl, any of which groups may be optionally substituted on the aromatic moiety;

$R^3$, $R^4$, and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, or —$CONR^aR^b$;

Z represents —$CH_2$— or —$CH_2CH_2$—;

$R^6$ represents hydrogen, $C_{1-6}$alkyl, $C_{1-6}$alkoxy, aryl, aryl ($C_{1-6}$)alkyl, or halogen; and $R^a$ and $R^b$ independently represent hydrogen, hydrocarbon, or a heterocyclic group.

The present invention also treats pain by a method of administering compounds of formula (I) as defined above, and salts and prodrugs thereof, wherein $R^2$ is other than an aryloxy($C_{1-6}$)alkyl group, optionally substituted on the aromatic moiety.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$alkyl, $C_{2-6}$alkenyl, $C_{2-6}$alkynyl, $C_{3-7}$cycloalkyl, $C_{3-7}$cycloalkyl($C_{1-6}$)alkyl, aryl, aryl($C_{1-6}$)alkyl, aryl($C_{2-6}$) alkenyl and aryl($C_{2-6}$)alkynyl.

The term "a heterocyclic group" as used herein includes cyclic groups containing up to 18 carbon atoms and at least one heteroatom, preferably oxygen, nitrogen, or sulfur. The heterocyclic group suitably contains up to 15 carbon atoms and conveniently up to 12 carbon atoms, and is preferably linked through carbon. Examples of suitable heterocyclic groups include $C_{3-7}$heterocycloalkyl, $C_{3-7}$heterocycloalkyl ($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

As used herein, "alkyl" as well as other groups having the prefix "alk" such as, for example, alkoxy, alkanoyl, alkenyl, alkynyl and the like, means carbon chains which may be linear or branched or combinations thereof. "Alkenyl", "alkynyl" and other like terms include carbon chains containing at least one unsaturated C—C bond.

Suitable alkyl groups within the scope of the term "hydrocarbon" and within the definition of the substituents R, $R^1$, and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, propyl, n-propyl, isopropyl, butyl, sec- and tert-butyl, pentyl, hexyl, and the like.

Suitable alkenyl groups within the scope of the term "hydrocarbon" and within the definition of the substituent $R^1$ include straight-chained and branched alkenyl groups containing from 2 to 6 carbon atoms. Typical examples include vinyl and allyl groups.

Suitable alkynyl groups within the scope of the term "hydrocarbon" and within the definition of the substituent $R^1$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

A particular aryl($C_{2-6}$)alkynyl group within the scope of the term "hydrocarbon" and within the definition of the substituents $R^1$ and $R^2$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$heterocycloalkyl($C_{1-6}$)alkyl group within the scope of the expression "a heterocyclic group" and within the definition of the substituent $R^1$ is tetrahydrofurylethyl.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl, and thiadiazolyl groups.

Particular heteroaryl($C_{1-6}$)alkyl groups within the scope of the expression "a heterocyclic group" and within the definition of the substituent $R^1$ include thienylmethyl, pyridylmethyl, pyrimidinylmethyl and pyrazinylmethyl.

Particular heteroaryl($C_{2-6}$)alkenyl groups within the scope of the expression "a heterocyclic group" and within the definition of the substituents $R^1$ and $R^2$ include furylethenyl and thienylethenyl.

The hydrocarbon and heterocyclic groups, as well as the substituents $R^1$ and $R^2$ may in turn be optionally substituted by one or more groups selected from $C_{1-6}$alkyl, adamantyl, phenyl, aryl($C_{1-6}$)alkyl, halogen, $C_{1-6}$haloalkyl, $C_{1-6}$aminoalkyl, trifluoromethyl, hydroxy, $C_{1-6}$alkoxy, aryloxy, keto, $C_{1-3}$alkylenedioxy, nitro, cyano, carboxy, $C_{2-6}$alkoxycarbonyl, $C_{2-6}$alkoxycarbonyl($C_{1-6}$)alkyl, $C_{2-6}$alkylcarbonyloxy, arylcarbonyloxy, $C_{2-6}$alkylcarbonyl, arylcarbonyl, $C_{1-6}$alkylthio, $C_{1-6}$alkylsuphinyl, $C_{1-6}$alkylsulphonyl, arylsulphonyl, trifluoromethanesulphonyloxy, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$PO(OR^v)(OR^w)$, —$CONR^vR^w$, —$SO_2NR^vR^w$, and —$CH_2SO_2NR^vR^w$, in which $R^v$ and $R^w$ independently represent hydrogen, $C_{1-6}$alkyl, aryl or aryl($_{1-6}$)alkyl.

The term "halogen" as used herein includes fluorine, chlorine, bromine, and iodine, especially chlorine.

The method of this invention includes using prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard. Elsevier, 1985.

The term "$C_0$" means that the carbon is not present. Thus, "$C_0$–$C_5$" means that there are from none to five carbons present—that is, five, four, three, two, one, or no carbons present.

The term "optionally substituted" is intended to include both substituted and unsubstituted. Thus, for example, optionally substituted aryl could represent a pentafluorophenyl or a phenyl ring.

Suitable, the substituent R represents hydrogen or methyl, especially hydrogen.

Suitable, the substitutent $R^1$ represents hydrogen.

As specified above, the substituent $R^2$ represents aryl, aryl($C_{1-6}$)alkyl, aryloxy($C_{1-6}$)alkyl, aryl($C_{1-6}$)alkyl, aryl($C_{1-6}$)alkoxy, aryl($C_{2-6}$)alkenyl, aryl($C_{2-6}$)alkynyl, heteroaryl or heteroaryl($C_{2-6}$)alkenyl, any of which groups may be optionally substituted on the aromatic moiety. Examples of optional substituents on the group $R^2$ include $C_{1-6}$alkyl, halogen, trifluoromethyl, $C_{1-6}$alkoxy, nitro, $C_{1-6}$alkylamino and di($C_{1-6}$)alkylamino.

Particular values of $R^2$ include phenyl, chlorophenyl, ethylphenyl, methoxyphenyl, nitrophenyl, benzyl, chlorobenzyl, phenethyl, phenylpropyl, phenoxymethyl, benzyloxy, phenylethenyl, methoxyphenylethenyl, phenylethynyl, benzofuryl, benzthienyl, furylethenyl, methyl-furylethenyl and thienylethenyl.

Suitable values for the substituents $R^3$, $R^4$, and $R^5$ include hydrogen, halogen, cyano, nitro, trifluoromethyl, amino, $C_{1-6}$alkylamino, di($C_{1-6}$)alkylamino, $C_{1-6}$alkyl, $C_{1-6}$alkoxy, aryl($C_{1-6}$)alkoxy, and $C_{2-6}$alkylcarbonyl. Particular values include hydrogen, fluoro, chloro, methyl, ethyl, methoxy and benzyloxy.

Particular values of $R^6$ include hydrogen, phenyl, chloro, and bromo.

Where the compounds described herein contain one or more asymmetric centers, such asymmetry gives rise to diastereomers and optical isomers. The present invention includes the utilization of any such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes the utilization of any stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound utilized by the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound utilized in the method of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions utilized by the present invention comprise a compound represented by Formula I (or pharmaceutically acceptable salts thereof) as an active ingredient, a pharmaceutically acceptable carrier and optionally other therapeutic ingredients or adjuvants. The utilized compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, utilized in the method of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the utilized compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions utilized in the method of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions utilized by the method of the present invention for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions utilized by the method of the present invention for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions utilized by the method of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions utilized by the method of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions utilized in the method of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds utilized in this invention.

Examples of compounds utilized in the method of this invention include:

2-(1,2,3,4-tetrahydroisoquinolin-2-ylmethyl)benzimidazole;

2-[4-(2-phenylethyl)piperidin-1-ylmethyl]benzimidazole;

2-(4-phenyl-1,2,3,6-tetrahydropyrid-1-ylmethyl)benzimidazole;

5-chloro-2-(1,2,3,4-tetrahydroisoquinolin-2-ylmethyl)benzimidazole;

5-methoxy-2-(1,2,3,4-tetrahydroisoquinolin-2-ylmethyl)benzimidazole;

2-(1,2-dihydroisoindol-2-ylmethyl)benzimidazole;

2-(4-benzylpiperidin-1-ylmethyl)benzimidazole;

2-(4-benzyl-1,2,3,6-tetrahydropyrid-1-ylmethyl)benzimidazole;

2-[4-(3-phenylpropyl)-1,2,3,6-tetrahydropyrid-1-ylmethyl]benzimidazole;

2-[4-(2-phenylethyl)-1,2,3,6-tetrahydropyrid-1-ylmethyl]benzimidazole;

2-[4-(2-phenylethynyl)-1,2,3,6-tetrahydropyrid-1-ylmethyl]benzimidazole;

2-(4-benzyloxy-1,2,3,6-tetrahydropyrid-1-ylmethyl)benzimidazole;

2-[4-(3-phenylpropyl)piperidin-1-ylmethyl]benzimidazole;

2-(4-benzyloxypiperidin-1-ylmethyl)benzimidazole;

2-[4-(3-phenylpropylidene)piperidin-1-ylmethyl]benzimidazole;

2-[4-(E)-(2-phenylethenyl)-1,2,3,6-tetrahydropyrid-1-ylmethyl]benzimidazole;

1-methyl-2-[4-(E)-(2-phenylethenyl)-1,2,3,6-tetrahydropyrid-1-ylmethyl]benzimidazole;

2-[4-(benzothiophen-2-yl)-1,2,3,6-tetrahydropyrid-1-ylmethyl]benzimidazole;

2-[4-(benzofuran-2-yl)-1,2,3,6-tetrahydropyrid-1-ylmethyl]benzimidazole;

2-[4-(E)-(2-thien-2-yl)ethenyl)-1,2,3,6-tetrahydropyrid-1-ylmethyl]benzimidazole;

2-[4-(E)-(2-(thien-3-yl)ethenyl)-1,2,3,6-tetrahydropyrid-1-ylmethyl]benzimidazole;

2-[4-(E)-(2-(furan-2-yl)ethenyl)-1,2,3,6-tetrahydropyrid-1-ylmethyl]benzimidazole;

2-[4-(E)-(2-(5-methylfuran-2-yl)ethenyl)-1,2,3,6-tetrahydropyrid-1-ylmethyl]benzimidazole;

2-[4-(E)-(2-(3-methoxyphenyl)ethenyl)-1,2,3,6-tetrahydropyrid-1-ylmethyl]benzimidazole;

2-(4-phenoxymethyl-1,2,3,6-tetrahydropyrid-1-ylmethyl)benzimidazole;

and salts and prodrugs thereof.

Experimental Protocols

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format at $3\times10^6$ cells per plate and grown for one—two days in normal growth media (Dulbeccos MEM with Na pyruvate, 4500 mgglucose, pen/strep, glutamine, 10% FCS and 0.5mg/ml geneticin). NR1A/2B-expression in these cells is induced by the addition of 4nM dexamethasone in the presence of 500 $\mu$M ketamine for 16–24 hours. After receptor induction cells are washed using a Labsystem Cellwasher two times with assay buffer (Hanks balanced salt solution (HBSS-Mg++ free) containing 20 M HEPES, 0.1% BSA, 2 mM $CaCl_2$ and 250$\mu$M probenecid). The cells of each 96 well cell plate are loaded with the Ca++ sensitive dye Fluo-3 (Molecular Probes, Inc.) at 4 $\mu$M in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 $\mu$l buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 $\mu$l agonist solution (final concentration 1 $\mu$M/1 $\mu$M) is then added by FLIPR into each well already containing 150 $\mu$l of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human NR1A/NR2B Receptors (Binding Assay):

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 $\mu$L of each of 10 solutions differing by 3-fold in concentration. Non-specific binding (NSB) using hot AMD-1 (10 $\mu$M final concentration) and total binding (TB) by using DMSO (2% final concentration). A solution of NR1A/NR2B receptors (40PM final concentration) and tritiated AMD-2 (1 nM final concentration) were added to the test compounds. After 3 h of incubation at room temperature, samples are filtered through Packard GF/B filters (presoaked in 0.05% PEI, polyetheninine Sigma P-3143) and washed 10 times with 1 mL of cold 20 mM Hepes buffer per wash. After vacuum drying of the filter plates, 40 $\mu$L of Packard Microscint-20 was added and bound radioactivity determined in a Packard TopCount. The apparent dissociation constant (Ki), the maximum percentage inhibition (%$I_{max}$), the minimum percentage inhibition (%$I_{min}$) and the hill slope (nH) were determined by a non-linear least squares fitting the bound CPM data to Equation #1 below.

Equation#1:

$$CPM\ Bound = \frac{(SB)(\%\,I_{max} - \%\,I_{min})}{(1+([Drug]/(Ki[L-844,345]/K_{DS}))^{nH})} + NSB + (SB)(1 - \%\,I_{max})$$

where, $K_D$ is the apparent dissociation constant for the radioligand for the receptor as determined by hot saturation and SB is the specifically bound CPM determined from the difference of TB and NSB.

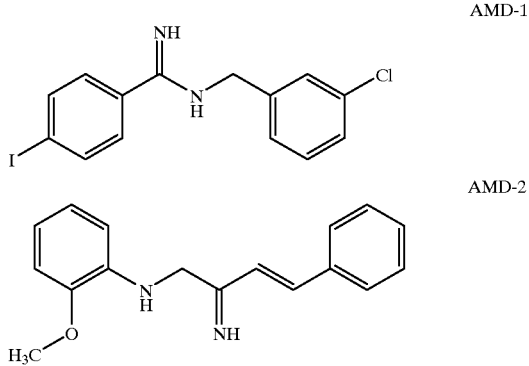

Compounds AMD-1 and AMD-2 can be synthesized in accordance with the following general reaction schemes.

SCHEME 1

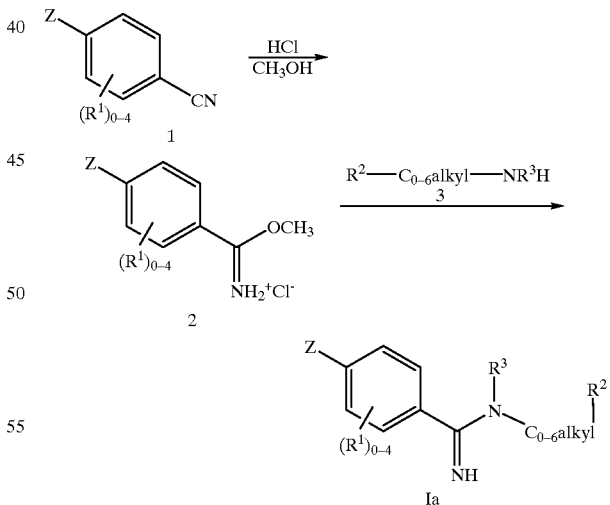

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

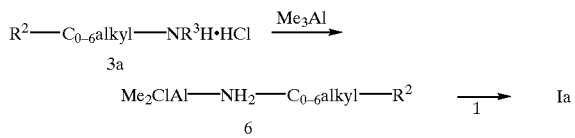

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I] AMD-1

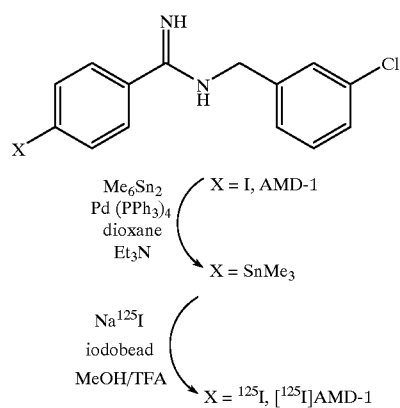

Tritiated AMD-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC (C18 Econosil, 10×250 mm, 20 minute linear gradient, 30% MeCN:70% H$_2$O (0.1% TFA) to 90% MeCN, 3 mL/min, 254 nm, retention time 15 minutes) to give 3 mg of the trimethylstannane.

A Na$^{125}$I shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C18 Vydac protein and peptide column, 4.6×250 mm, 20 minute linear gradient, 30% MeCN:70% H$_2$O (0.1% TFA) to 90% MeCN, 1 mL/min, retention time 11 minutes). Fractions containing the radioactive product were pooled and concentrated in vacuo to give 989 μCi of [$^{125}$I]AMD-1 with a specific activity of 898 Ci/mmol as measured by UV absorbance at 272nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potasium carbonate (1.2 mg) for 1 hr. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.45 μm syringeless filter device to remove any insoluable potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetronitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit less than 50 μM in the FLIBR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

What is claimed is:

1. A method to treat pain, or migraine, said method comprising a step of administering to one in need of such treatment an effective amount of an NMDA NR2B antagonist described by formula (I):

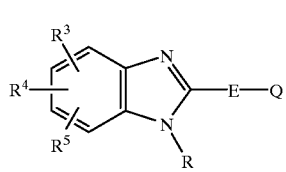

or a salt or prodrug thereof, wherein

E represents —CH$_2$— or —CH$_2$CH$_2$—;

R represents hydrogen or C$_{1-6}$alkyl;

Q represents a moiety of formula Qa, Qb, or Qc:

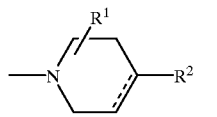
(Qa)

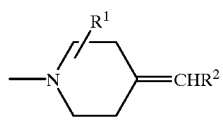
(Qb)

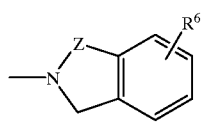
(Qc)

in which the broken line represents an optional chemical bond;

$R^1$ represents hydrogen, or an optionally substituted $C_{1-6}$alkyl, $C_{1-6}$alkoxy, $C_{2-6}$alkenyl, $C_{2-6}$alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an aryl, aryl($C_{1-6}$)alkyl, aryloxy($C_{1-6}$)alkyl, aryl($C_{1-6}$)alkyl, aryl($C_{1-6}$)alkoxy, aryl($C_{2-6}$)alkenyl, aryl($C_{2-6}$)alkynyl, heteroaryl or heteroaryl($C_{2-6}$) alkenyl group, any of which groups may be optionally substituted on the aromatic moiety;

$R^3$, $R^4$, and $R^5$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$, or $-CONR^aR^b$;

Z represents $-CH_2-$ or $-CH_2CH_2-$;

$R^6$ represents hydrogen, $C_{1-6}$alkyl, $C_{1-6}$alkoxy, aryl, aryl ($C_{1-6}$)alkyl, or halogen; and $R^a$ and $R^b$ independently represent hydrogen, hydrocarbon, or a heterocyclic group.

2. The method according to claim 1, wherein said NMDA NR2B antagonist is 2-(1,2,3,4-tetrahydroisoquinolin-2-ylmethyl) benzimidazole;

2-[4-(2-phenylethyl)piperidin-1-ylmethyl]benzimidazole;

2-(4-phenyl-1,2,3,6-tetrahydropyrid-1-ylmethyl) benzimidazole;

5-chloro-2-(1,2,3,4-tetrahydroisoquinolin-2-ylmethyl) benzimidazole;

5-methoxy-2-(1,2,3,4-tetrahydroisoquinolin-2-ylmethyl) benzimidazole;

2-(1,2-dihydroisoindol-2-ylmethyl)benzimidazole;

2-(4-benzylpiperidin-1-ylmethyl)benzimidazole;

2-(4-benzyl-1,2,3,6-tetrahydropyrid-1-ylmethyl) benzimidazole;

2-[4-(3-phenylpropyl)-1,2,3,6-tetrahydropyrid-1-ylmethyl]benzimidazole;

2-[4-(2-phenylethyl)-1,2,3,6-tetrahydropyrid-1-ylmethyl] benzimidazole;

2-[4-(2-phenylethynyl)-1,2,3,6-tetrahydropyrid-1-ylmethyl]benzimidazole;

2-(4-benzyloxy-1,2,3,6-tetrahydropyrid-1-ylmethyl) benzimidazole;

2-[4-(3-phenylpropyl)piperidin-1-ylmethyl] benzimidazole;

2-(4-benzyloxypiperidin-1-ylmethyl)benzimidazole;

2-[4-(3-phenylpropylidene)piperidin-1-ylmethyl] benzimidazole;

2-[4-(E)-(2-phenylethenyl)-1,2,3,6-tetrahydropyrid-1-ylmethyl]benzimidazole;

1-methyl-2-[4-(E)-(2-phenylethenyl)-1,2,3,6-tetrahydropyrid-1-ylmethyl]benzimidazole;

2-[4-(benzothiophen-2-yl)-1,2,3,6-tetrahydropyrid-1-ylmethyl]benzimidazole;

2-[4-(benzofuran-2-yl)-1,2,3,6-tetrahydropyrid-1-ylmethyl]benzimidazole;

2-[4-(E)-(2-thien-2-yl)ethenyl)-1,2,3,6-tetrahydropyrid-1-ylmethyl]benzimidazole;

2-[4-(E)-(2-(thien-3-yl)ethenyl)-1,2,3,6-tetrahydropyrid-1-ylmethyl]benzimidazole;

2-[4-(E)-(2-(furan-2-yl)ethenyl)-1,2,3,6-tetrahydropyrid-1-ylmethyl]benzimidazole;

2-[4-(E)-(2-(5-methylfuran-2-yl)ethenyl)-1,2,3,6-tetrahydropyrid-1-ylmethyl]benzimidazole;

2-[4-(E)-(2-(3-methoxyphenyl)ethenyl)-1,2,3,6-tetrahydropyrid-1-ylmethyl]benzimidazole; or 2-(4-phenoxymethyl-1,2,3,6-tetrahydropyrid-1-ylmethyl) benzimidazole;

or salts and prodrugs thereof.

* * * * *